United States Patent
Riley et al.

(10) Patent No.: US 7,229,548 B2
(45) Date of Patent: Jun. 12, 2007

(54) PROCESS FOR UPGRADING NAPHTHA

(75) Inventors: Kenneth L. Riley, Baton Rouge, LA (US); Stuart L. Soled, Pittstown, NJ (US); Sabato Miseo, Pittstown, NJ (US); Frans L. Plantenga, Hoevelaken (NL); Marinus Bruce Cerfontain, Amsterdam (NL); Sonja Eijsbouts, Nieuwkuijk (NL); Eelko Brevoord, Hoevelaken (NL)

(73) Assignee: ExxonMobil Research and Engineering Company, Annadale, NJ (US)

( * ) Notice: Subject to any disclaimer, the term of this patent is extended or adjusted under 35 U.S.C. 154(b) by 507 days.

(21) Appl. No.: 10/677,697

(22) Filed: Oct. 2, 2003

(65) Prior Publication Data

US 2005/0040080 A1    Feb. 24, 2005

Related U.S. Application Data

(63) Continuation-in-part of application No. 09/869,984, filed on Aug. 22, 2001, which is a continuation-in-part of application No. 09/231,156, filed on Jan. 15, 1999, now Pat. No. 6,162,350, which is a continuation-in-part of application No. 08/900,389, filed on Jul. 15, 1997, now Pat. No. 6,156,695.

(51) Int. Cl.
*C10G 45/00* (2006.01)
*C10G 65/02* (2006.01)

(52) U.S. Cl. .................. 208/216 R; 208/89; 208/113; 208/143; 208/210; 208/213; 208/216; 208/216 PP; 208/217; 208/254 H; 502/220; 585/269

(58) Field of Classification Search .................. 208/89, 208/113, 143, 210, 213, 216, 216 PP, 216 R, 208/217, 254 H; 502/220, 305; 585/269
See application file for complete search history.

(56) References Cited

U.S. PATENT DOCUMENTS 2,690,433 A    7/1952    Engel et al.

(Continued)

FOREIGN PATENT DOCUMENTS

CN    1218088    6/1999

(Continued)

OTHER PUBLICATIONS

Levin, Doron, et al., "Crystal Structure of an Ammonium Nickel Molybdate Prepared by Chemical Precipitation," *Inorganic Chemistry*, 1996, 35, pp. 4191-4197 (Sep. 1995).

(Continued)

*Primary Examiner*—Glenn Caldarola
*Assistant Examiner*—Prem C. Singh
(74) *Attorney, Agent, or Firm*—H. E. Naylor; Gerard J. Hughes (57) ABSTRACT

A method for upgrading a naphtha feed to a naphtha product containing less than about 10 wppm of nitrogen and less than about 15 wppm sulfur, the method comprising contacting said naphtha feed with hydrogen in the presence of a bulk multimetallic catalyst under effective reactor conditions to hydrodesulfurize and hydrodenitrogenize said naphtha feed to produce said naphtha product, wherein said bulk multimetallic catalyst comprises at least one Group VIII non-noble metal and at least two Group VIB metals.

25 Claims, 4 Drawing Sheets

U.S. PATENT DOCUMENTS

| | | | |
|---|---|---|---|
| 2,873,257 A | 2/1959 | Hunter et al. | |
| 2,946,738 A | 7/1960 | Gardner et al. | |
| 3,198,753 A | 8/1965 | Traina | |
| 3,280,040 A | 10/1966 | Jaffe | |
| 3,408,309 A | 10/1968 | Gessner | |
| 3,520,796 A | 7/1970 | Murphy, Jr. et al. | |
| 3,619,414 A * | 11/1971 | Mills et al. | 208/143 |
| 3,678,124 A | 7/1972 | Stepanov et al. | |
| 3,850,746 A | 11/1974 | Robson | |
| 3,861,005 A | 1/1975 | Steinmetz et al. | |
| 3,901,828 A | 8/1975 | Mai et al. | |
| 3,925,197 A | 12/1975 | Van Klinken et al. | |
| 3,959,179 A | 5/1976 | Mikovsky et al. | |
| 4,013,545 A | 3/1977 | Hilfman | |
| 4,014,925 A | 3/1977 | Ferlazzo et al. | |
| 4,113,603 A | 9/1978 | Bauer | |
| 4,113,605 A | 9/1978 | Mickelson | |
| 4,153,578 A | 5/1979 | De Thomas et al. | |
| 4,181,602 A | 1/1980 | Quick et al. | |
| 4,388,223 A | 6/1983 | Ferlazzo et al. | |
| 4,392,945 A | 7/1983 | Howard et al. | |
| 4,491,639 A | 1/1985 | Happel et al. | |
| 4,596,785 A | 6/1986 | Toulhoat et al. | |
| 4,701,381 A | 10/1987 | Jack | |
| 4,720,477 A | 1/1988 | Hettinger, Jr. | |
| 4,721,558 A | 1/1988 | Jacobson et al. | |
| 4,748,142 A | 5/1988 | Chianelli et al. | |
| 4,808,563 A | 2/1989 | Velenyi | |
| 4,820,677 A | 4/1989 | Jacobson et al. | |
| 4,824,821 A | 4/1989 | Lopez et al. | |
| 4,857,496 A | 8/1989 | Lopez et al. | |
| 4,875,992 A | 10/1989 | Hamner | |
| 4,902,404 A | 2/1990 | Ho | |
| 5,112,472 A | 5/1992 | Gosselink et al. | |
| 5,122,258 A | 6/1992 | Eadie et al. | |
| 5,244,858 A | 9/1993 | Usui et al. | |
| 5,252,199 A | 10/1993 | Singhal et al. | |
| 5,292,428 A | 3/1994 | Harrison et al. | |
| 5,320,741 A | 6/1994 | Johnson et al. | |
| 5,446,004 A | 8/1995 | Tenten et al. | |
| 5,565,091 A | 10/1996 | Iino et al. | |
| 5,643,441 A | 7/1997 | Timken et al. | |
| 5,841,013 A * | 11/1998 | Ho et al. | 585/269 |
| 5,851,382 A | 12/1998 | Sudhakar | |
| 5,865,988 A | 2/1999 | Collins et al. | |
| 5,968,346 A | 10/1999 | Jung et al. | |
| 5,993,643 A | 11/1999 | Chang et al. | |
| 6,002,919 A | 12/1999 | Posti | |
| 6,071,402 A | 6/2000 | Danot et al. | |
| 6,083,378 A | 7/2000 | Gildert et al. | |
| 6,156,694 A | 12/2000 | Harper | |
| 6,156,695 A | 12/2000 | Soled et al. | |
| 6,162,350 A * | 12/2000 | Soled et al. | 208/113 |
| 6,162,351 A | 12/2000 | Sudhakar et al. | |
| 6,231,750 B1 | 5/2001 | Kasztelan et al. | |
| 6,231,753 B1 | 5/2001 | McKnight et al. | |
| 6,256,695 B1 | 7/2001 | Williams | |
| 6,582,590 B1 * | 6/2003 | Riley et al. | 208/210 |
| 6,712,955 B1 * | 3/2004 | Hou et al. | 208/216 R |
| 2001/0000006 A1 | 3/2001 | Kasztelan et al. | |
| 2003/0102254 A1 | 6/2003 | Eijsbouts et al. | |

FOREIGN PATENT DOCUMENTS

| | | |
|---|---|---|
| CZ | 158758 A | 7/1975 |
| DE | 3029266 C2 | 8/1980 |
| EP | 0203228 A1 | 7/1985 |
| EP | 0183353 B1 | 9/1985 |
| EP | 0215989 A1 | 9/1985 |
| EP | 0244106 B1 | 4/1987 |
| EP | 0277718 A2 | 1/1988 |
| EP | 0379433 A1 | 1/1990 |
| EP | 0419266 A1 | 9/1990 |
| EP | 0469675 B1 | 7/1991 |
| EP | 0590672 A1 | 9/1993 |
| EP | 0590673 A1 | 9/1993 |
| EP | 0635555 A2 | 7/1994 |
| EP | 0685260 A2 | 5/1995 |
| EP | 0849351 B1 | 12/1997 |
| EP | 0900929 B1 | 9/1998 |
| GB | 1282950 | 2/1970 |
| GB | 1458887 | 7/1974 |
| RU | 2030444 C1 | 7/1992 |
| WO | WO 99/03578 | 1/1999 |
| WO | WO 99/41327 | 8/1999 |
| WO | WO 00/41810 | 7/2000 |
| WO | WO 00/41881 | 7/2000 |
| WO | WO 00/42119 | 7/2000 |
| WO | WO 00/42125 | 7/2000 |
| WO | WO 00/42131 | 7/2000 |

OTHER PUBLICATIONS

Mazzocchia, C., et al., "On the NiO MoO3 mixed oxide correlation between preparative procedures thermal activation and catalytic properties," *Solid State Ionics*, 63-65 (1993) pp. 731-735.

Astier, M.P., et al., "Nickel-molybdenum catalysts prepared by reduction of ammonium triamine tetranickel pentamolybdate," *Applied Catalysts*, 72 (1991) pp. 321-329.

Olah, George A., Hydrocarbon Chemistry, 1995, p. 30.

Astier, M.P., et al., "Ammonium Triammine Tetranickel Pentamolybdate Preparation, Characterization and Crystal Structure," *Ann. Chem. Fr.*, 12, pp. 337-343 (1987).

Astier, M.P., et al., "Solid State Chemistry," *C.R. Acad. Sc. Paris.*, 304, (II), No. 11, pp. 563-566 (1987).

Mazzocchia, C., et al., "On the NiMoO4 oxidative dehydrogenation of propane to propene: some physical correlations with the catalytic activity," *Catalysis Letters* 10 (1991) pp. 181-192.

Levin, Doron, et al., "*Chemie Douce* Synthesis of a Layered Ammonium Zinc Molybdate," *Chem. Mater.* 1996, 8, pp. 836-843.

M. Daage, et al., "Structure-Function Relations in Molybdenum Sulfide Catalysts: The "Rim-Edge" Model", *Journal of Catalysts*, 149, 414-427 (1994).

* cited by examiner

# PROCESS FOR UPGRADING NAPHTHA

CROSS REFERENCE TO RELATED APPLICATIONS

This is a continuation-in-part of U.S. Ser. No. 09/869,984 filed on Aug. 22, 2001, which is a continuation-in-part of U.S. Ser. No. 09/231,156 filed on Jan. 15, 1999 now U.S. Pat. No. 6,162,350 issued Dec. 19, 2000, which is a continuation-in-part of U.S. Ser. No. 08/900,389 which was filed on Jul. 15, 1997 and which issued as U.S. Pat. No. 6,156,695 on Dec. 5, 2000, all of which are incorporated herein by reference for all purposes to the extent that they are not inconsistent with the disclosure and claims of the present invention.

FIELD OF THE INVENTION

This invention relates generally to an improved hydroprocessing method for upgrading a naphtha feed using a bulk multimetallic catalyst ("BMC").

BACKGROUND OF THE INVENTION

Environmental and regulatory initiatives require lower levels of sulfur, nitrogen, and aromatics in distillate fuels and lubes products. For example, for distillate fuels, sulfur limits of 10–15 wppm (weight parts per million) or less have been proposed.

A major contributor to sulfur in the gasoline pool, is naphtha from fluid catalytic cracking (FCC) units. Naphtha gasoline contains high amounts of olefinic and aromatic compounds, and a relatively high amount of nitrogen and sulfur.

Some are developing technologies designed to reduce sulfur without a significant octane loss, caused by olefins saturation. Others consider hydrotreating some of the FCC naphtha to very low sulfur and nitrogen levels (<0.5 wppm) and increasing the octane number of the naphtha by reforming. This approach is of particular interest with naphthas having a relatively low octane number. Fractions to be fed to catalytic reforming need to be desulfurized before reforming because reforming catalysts are generally not tolerant to sulfur.

In U.S. Pat. No. 5,346,609 and U.S. Pat. No. 5,409,596 (Ser. No. 08/850,106), we have described a process for effectively desulfurizing catalytically cracked naphthas while maintaining a high octane number. Briefly, the process comprises an initial hydrodesulfurization step which reduces the sulfur to an acceptable level, although at the expense of octane which is restored in a subsequent step by treatment over an acidic catalyst such as one based on ZSM-5, as described in U.S. Pat. No. 5,346,609 and U.S. Pat. No. 5,490,596 (Ser. No. 08/850,106), zeolite beta as described in Ser. No. 07/891,124 (now U.S. Pat. No. 5,413,696) or MCM-22 as described in U.S. Pat. No. 5,352,354.

SUMMARY OF THE INVENTION

The present invention relates generally to an improved hydroprocessing method and catalyst for treating naphtha feeds. The method comprises contacting a naphtha feed at hydroprocessing conditions, with a catalyst composition comprising at least one Group VIII non-noble metal and at least two Group VIB metals. The catalyst composition is preferably made by contacting and reacting insoluble or partially insoluble metal salts of the catalyst metals in the presence of a protic liquid. Alternatively at least one of the metal salts should remain at least partly in the solid state during the entire process. However, the catalyst may also be made by reacting metal salts of the catalyst metals which are all in the dissolved state. The method may include hydrodesulfurization, hydrodenitrogenation, hydrodemetallation, hydrodearomatization, hydroisomerization, hydrodewaxing and hydrocracking.

One embodiment of the present invention relates to a method for upgrading a naphtha feed containing high amounts of sulfur and nitrogen compounds to a naphtha product containing less than about 10 wppm of nitrogen and less than about 15 wppm sulfur, the method comprising contacting said naphtha feed with hydrogen in the presence of a bulk multimetallic catalyst under effective reactor conditions to hydrodesulfurize and hydrodenitrogenize said naphtha feed to produce said naphtha product, wherein said bulk multimetallic catalyst comprises at least one Group VIII non-noble metal and at least two Group VIB metals.

Another embodiment of the present invention relates to a method for upgrading a naphtha feed to a naphtha product containing less than about 10 wppm of nitrogen and less than about 15 wppm sulfur, the method comprising reacting said naphtha in at least one reaction stage, in the presence of a hydrogen containing gas, as it passes through two or more catalyst beds wherein at least one catalyst bed comprises a multimetallic catalyst comprising at least one Group VIII non-noble metal and at least two Group VIB metals wherein the ratio of Group VIB metals to Group VIII non-noble metals is preferably about 10:1 to about 1:10, wherein said at least one reaction stage is operated at effective reactor conditions to hydrodesulfurize and hydrodenitrogenize the naphtha feed to produce said naphtha product. More preferably the naphtha feed is upgraded to a naphtha product containing less than about 5 wppm sulfur and less than about 5 wppm nitrogen.

Various naphtha feeds may be used such as light and full range virgin naphthas, catalytically cracked naphthas, delayed coking naphtha, fluid coking naphtha and contact coking naphtha.

DETAILED DESCRIPTION OF THE INVENTION

The present invention relates generally to improved hydroprocessing methods. More particularly, it relates to a method comprising treating naphtha under hydroprocessing reaction conditions with a bulk multimetallic catalyst. Suitable temperature may generally range from about 200° C. to about 450° C., hydrogen pressure may range from about 5 to about 300 bar, liquid hourly space velocities from about 0.05 to about 10 h$^{-1}$, and the hydrogen treat gas rate may range from about 17.8 to about 1780 m$^3$/m$^3$ of hydrocarbon feed (100 to 10,000 SCF/B). The term "hydroprocessing" encompasses all processes in which a hydrocarbon feed is reacted with hydrogen at the conditions noted above, and may include hydrodemetallation, hydrodewaxing, hydrotreating, hydrogenation, hydrodesulfurization, hydrodenitrogenation, hydrodearomatization, hydroisomerization, and hydrocracking. Hydrocracking may include selective hydrocracking and mild hydrocracking. In addition to lower heteroatom amounts, depending on the type of hydroprocessing and the reaction conditions, the products may also show improved viscosities, viscosity indices, saturates content, low temperature properties, volatilities and depolarization. Hydroprocessing may be practiced in one or more stages, each stage having one or more reaction zones. It may be practiced in countercurrent flow or concurrent flow mode of operation. In a countercurrent flow mode a hydrocarbon feed flows countercurrent to the flow of a hydrogen-containing treat gas. Each reactor can be a fixed bed, slurry bed, ebulating bed, or any of many well-known types of catalytic reactors and combinations thereof.

Figure 1:
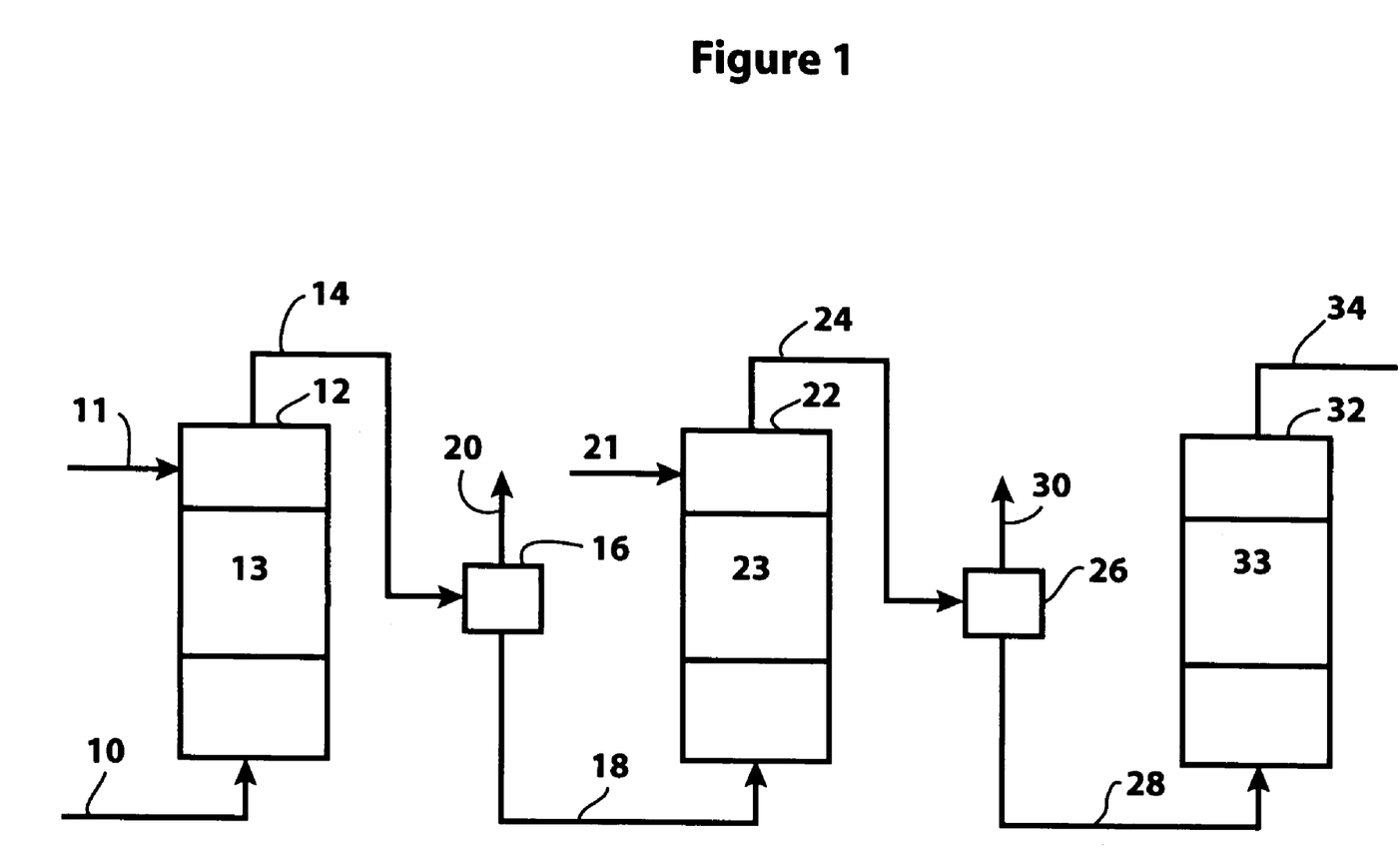
FIG. 1 is a simplified schematic of an embodiment of the present invention method.

Referring now to FIG. 1, one embodiment of the present invention includes feeding a hydrocarbon feedstock 10 containing high levels of sulfur and nitrogen to a first hydrodesulfurization ("HDS") and hydrodenitrogenation ("HDN") reaction stage 12 to remove a substantial amount of the sulfur and nitrogen. For example, the inventive method is particularly suitable for upgrading naphtha feeds containing high amounts of sulfur including those containing high amounts of sulfur more than about 3,000 wppm sulfur. According to a preferred embodiment, the feed is hydrodesulfurized and hydrodenitrogenized in a first stage 12, which may contain one or more reaction zones 13, in the presence of hydrogen or hydrogen containing treat gas 11, and a first hydrotreating catalyst under effective HDS and/or HDN conditions.

The catalyst comprises at least one Group VIII non-noble metal and at least two Group VIB metals, and is preferably made by contacting and reacting insoluble or partially insoluble metal salts of the catalyst metals in the presence of a liquid. Preferably, the ratio of Group VIB metal to Group VIII metal may range from about 10:1 to about 1:10. More details of the catalyst composition and suitable methods of preparation may be found in U.S. Pat. No. 6,162,350, U.S. Pat. No. 6,156,695, U.S. Pat. No. 6,299,760, and PCT published applications WO 00/41810 and WO 00/41811, which are incorporated herein by reference for all purposes to the extent that they are not inconsistent with the present invention.

The product stream 14 is passed to a first separation zone 16 wherein a vapor phase stream 20 and a liquid phase stream 18 are produced. The liquid phase product stream 18 is passed to a second HDS and/or HDN stage 22, which also may contain one or more reaction zones, where it is further hydrodesulfurized in the presence of hydrogen 21 and a second catalyst 23. The second catalyst 23 may be identical to the first catalyst 13, modified, or different. For example, a conventional HDS and/or HDN catalyst may be used in the second stage, or an admixture of a conventional catalyst with the preferred bulk multimetallic catalyst of the present invention. The liquid product stream 24 from the second hydrodesulfurization 23 stage is passed to a second separation zone 26 wherein a vapor product stream 30 is collected for further processing or blending. A liquid product stream 28 is passed to a third reaction stage 32 which is operated in the presence of a hydrogenation catalyst 33. At least a portion of the vapor product streams, e.g., 20, 30, or both, from any reaction stage may be recycled to the first reaction stage or subsequent stages.

Optionally, at least a portion of the vapor product streams from the separation zones 16 and 26 may be recycled to the first or subsequent stages. For example, at least a portion of the vapor product stream 30 from the second separation stage 26 may be recycled to the first stage 12.

The second stage 22 may be operated under the same or somewhat different process conditions than the first stage.

The feed 10 is preferably a naphtha feed, more preferably a naphtha feed from a catalytic cracker. Other preferred feeds include a distillate boiling range feed from an atmospheric distillation tower, such as a raw virgin petroleum distillate. The product stream 14 contains substantially less sulfur than the feed 10. The precise amount of sulfur may vary depending upon the amount of sulfur in the feed 10, the process conditions, and the catalyst used. According to one embodiment, the sulfur in the product stream 14 is less than about 750 wpm, preferably less than about 150 wppm, and more preferably less than about 50 wppm, and most preferably less than about 15 wppm. Hydrodenitrogenation may also occur in the first stage 12. Preferably the product stream may contain 300 wppm nitrogen or less, typically from about 15 to about 150 wppm. If more than one reaction zone is used in each stage, it is preferred that at least one of the reaction zones contains a bed of the preferred multimetallic catalyst. For example, the first stage reactor stage may contain a stacked bed arrangement wherein a conventional hydrodesulfurization catalyst comprises one or more reaction zones and the preferred multimetallic catalyst of the present invention comprises the other one or more reaction zones. Also preferably, if a conventional hydrodesulfurization catalyst and a preferred catalyst are used in a single stage, the conventional catalyst may be used in the upstream reaction zone or zones.

The second stage 22 also may contain one or more reaction zones. Like the first stage, the second stage 22 may contain one or more reaction zones preferably with at least one reaction zone containing the preferred multimetallic catalyst of the invention. If present, other catalyst or catalysts can be conventional HDS and/or HDN catalysts. If a conventional catalyst is used, it is preferred to be present upstream of the preferred multimetallic catalyst. The liquid phase product stream 28 from the second stage separator 26 may contain less than about 150 wppm, preferably less than about 50 wppm, more preferably less than about 15 wppm sulfur, and most preferably less than about 5 wppm. The hydrodesulfurized liquid product stream 28 may optionally be passed to a third hydroprocessing reaction stage 32 for further treatment. For example, it may be reacted in the presence of hydrogen and a catalyst 33 capable of further reducing the heteroatoms levels and hydrogenating the aromatics in the product. Alternatively, stage 32 may contain a hydrocracking catalyst. Other variations may be readily envisioned by a person with ordinary skill in this art. The sulfur level of the final product stream 34 is preferably less than about 15 wppm, more preferably less than about 10 wppm, and most preferably less than about 5 wppm. The nitrogen level of the final product stream 34 is preferably less than about 10 wppm, more preferably less than about 5 wppm, and most preferably less than about 1 wppm. Reaction stage 32 may also contain multiple reaction zones, however, preferably, in at least one reaction zone may contain a hydrogenation catalyst and optionally the preferred bulk multimetallic catalyst of the present invention. When sulfur intolerant conventional catalysts are employed, such as platinum or noble metal catalysts, the preferred bulk multimetallic catalyst of the present invention should be upstream the conventional catalyst since it is more tolerant to sulfur.

Where conventional catalysts are used, one or more of the reaction zones of any or both of the stages may contain one or more conventional HDS and/or HDN catalysts. Suitable conventional catalysts for use in the present invention includes those that are comprised of at least one Group VIII metal, preferably Fe, Co or Ni, more preferably Co and/or Ni, and most preferably Co; and at least one Group VI metal, preferably Mo or W, more preferably Mo, on a relatively high surface area support material, preferably alumina. Other suitable supports include zeolites, amorphous silica-alumina, and titania-alumina noble metal catalysts can also be employed, preferably where the noble metal is selected from Pd, Pt, and mixtures thereof. It is within the scope of the present invention that more than one type of catalysts be used in the same reaction vessel. For conventional catalysts, the Group VIII metal is typically present in an amount ranging from about 2 to about 20 wt. %, preferably from about 2 to about 12 wt. %, more preferably from about 2 to about 6 wt. %, and most preferably from about 2 to about 3 wt. %. The Group VI metal is typically present in an amount ranging from about 5 to about 50 wt. %, preferably from about 10 to about 40 wt. %, and more preferably from about 15 to about 26 wt. %. For hydrotreating catalyst applications, Group VIII metal may be present in an amount of from about 4 to about 6 wt. %, and Group VI metal may be present in an amount of from about 20 to about 26 wt. %. In an embodiment where the hydrotreating catalyst is used for naphtha treatment, the catalyst may have lower levels of Group VIII and Group VI metals, such as 2 to about 3 wt. % and 6 to about 10 wt. %, respectively. All metal weight percents are based on the weight of the support. The catalysts can be used in the spent, regenerated, or fresh state. The amounts of hydrogenation metal components are calculated as oxides.

Different catalyst arrangements for the three reaction stage process of FIG. 1 can be:
(a) a preferred multimetallic catalyst of this invention in either or both of the first two reaction stages but not the third;
(b) a conventional hydrodesulfurization catalyst in the first two reaction stages and only the preferred bulk multimetallic catalyst in the third reaction stage;
(c) the bulk multimetallic catalyst in either the first two reaction stages and also in the third reaction stage along with the hydrogenation catalyst; and
(d) all three reaction stages have at least one reaction zone containing the bulk multimetallic catalyst.

Figure 2:
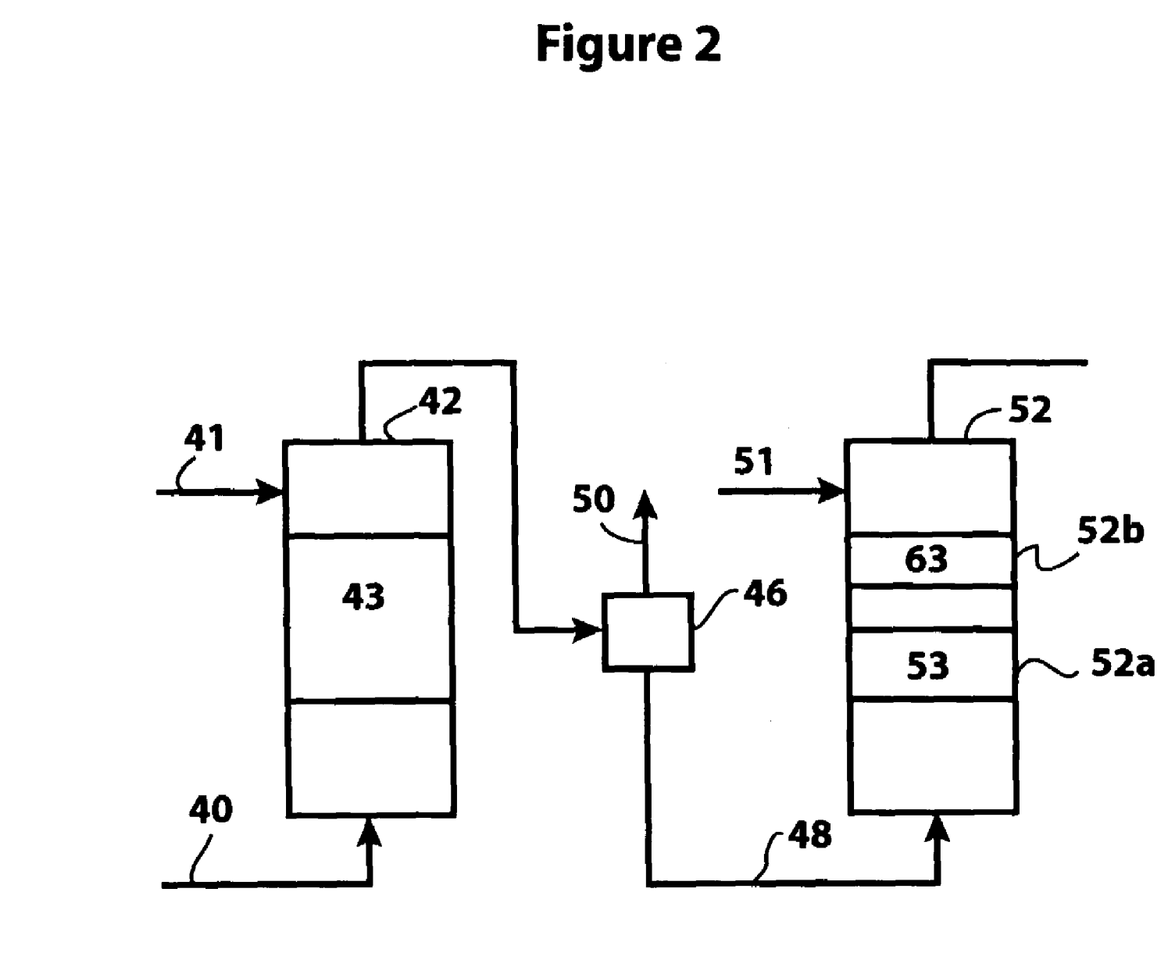
FIG. 2 is a simplified schematic of another embodiment of the present invention method.

In yet another embodiment of the present invention, shown in FIG. 2, only two reaction stages 42 and 52 are used. The feed 40 to the first reaction stage 42 may be the same feed as for the three reaction stage process. Reaction stage 42 can contain a conventional hydrodesulfurizatioin catalyst, the bulk multimetallic catalyst, or both. The product stream 48 from the first stage 42 will preferably contain from about 100 to about 1,500 wppm, more preferably from about 100 to about 1,000 wppm, and most preferably from about 100 to about 750 wppm sulfur. The product stream 48 may also contain nitrogen preferably in an amount from about 10 to about 300 wppm nitrogen, more preferably from about 10 to about 150 wppm, and most preferably from about 10 to about 100 wppm nitrogen. The second reaction stage 52 may contain both a preferred bulk multimetallic catalyst 53 as well as an aromatic hydrogenation catalyst 63. Each catalyst may be placed in a different reaction zone with the preferred bulk multimetallic catalyst 53 placed in the first reaction zone 52a and the aromatic hydrogenation catalyst placed in the second reaction zone 52b downstream said multimetallic catalyst 63. The final product stream will preferably contain less than about 15 wppm, more preferably less than about 10 wppm sulfur and a substantially lower level of aromatics, preferably less than about 15 wppm aromatics. Also, preferred by the nitrogen level in the final product will be less than about 10 wppm, more preferably less than about 5 wppm.

Non-limiting examples of aromatic hydrogenation catalysts include nickel, cobalt-molybdenum, nickel-molybdenum, and nickel tungsten. Carriers may be used such as the ones used for noble metal catalysts. Non-limiting examples of noble metal catalysts include those based on platinum and/or palladium, which is preferably supported on a suitable support material, typically a refractory oxide material such as alumina, silica, alumina-silica, kieselguhr, diatomaceous earth, magnesia, and zirconia. Zeolitic supports can also be used. Such catalysts are typically susceptible to sulfur and nitrogen poisoning. The aromatic saturation zone is preferably operated at a temperature from about 40° C. to about 400° C., more preferably from about 260° C. to about 350° C., at a pressure from about 100 psig to about 3,000 psig, preferably from about 200 psig to about 1,200 psig, and at a liquid hourly space velocity (LHSV) of from about 0.3 V/V/hr to about 2.0 V/V/hr.

Process conditions applicable for the use of the catalysts described herein may vary widely depending on the feedstock to be treated. Thus, as the boiling point of the feed increases, the severity of the conditions will also increase. The following table serves to illustrate typical HDS and HDN conditions for a naphtha feed. The hydrogen treat gas should have a purity of 50% to 100% by volume.

| Naphtha Feed | Typical Boiling Range, ° C. | Temperature, ° C. | Pressure, Bar | Space Velocity V/V/hour | H₂ Gas Rate, SCF/B |
| --- | --- | --- | --- | --- | --- |
| Broad | 10–232 | 100–370 | 10–60 | 0.5–15 | 100–5,000 |
| Preferred | 30–220 | 260–355 | 13–35 | 0.5–10 | 200–2,500 |

One embodiment of the present invention relates to a method for upgrading naphtha. The method comprises contacting a naphtha feed that is high in sulfur, and nitrogen compounds, with hydrogen in the presence of a bulk multimetallic catalyst. The catalyst comprises at least one Group VIII non-noble metal and at least two Group VIB metals. The catalyst is preferably made by reacting insoluble or partially insoluble metal salts of the metals in the presence of a protic liquid. Preferably, at least one of the metal components remains at least partly in the solid state during the entire catalyst making process. Also, preferably the Group VIII and Group VIB metals comprise from about 50 wt. % to about 100 wt. %, calculated as oxides, of the total weight of the bulk catalyst particles. The solubility of those metal components which are at least partly in the solid state during the reaction process being preferably less than about 0.05 mol/100 ml water at 18° C. The catalyst is preferably sulfided prior to use in the hydrotreating step. The referred catalyst compositions of the present invention and the preferred methods of making them are described in more detail in U.S. Pat. No. 6,156,695, U.S. patent application Ser. No. 09/836,101, and PCT published applications WO 00/41810 and WO 00/41811, which are incorporated herein by reference for all purposes to the extent that they are not inconsistent with the present invention disclosure and claims.

The catalyst used in the process of the invention is a bulk catalyst comprising at least one Group VIII non-noble metal component and at least two Group VIB metal components.

In the context of the present specification, the wording "metal component" refers to a salt, oxide, sulfide, or any intermediate form between oxide and sulfide of the metal in question. As will be evident to the skilled person, the wording "at least two Group VIB metal components" is intended to refer to components of at least two Group VIB metals, e.g., the combination of molybdenum and tungsten.

The indications Group VIB and Group VIII used in the present specification correspond to the Periodic Table of Elements applied by Chemical Abstract Services (CAS system).

Suitable Group VIB metals include chromium, molybdenum, tungsten, or mixtures thereof, with a combination of molybdenum and tungsten being preferred. Suitable Group VIII non-noble metals include iron, cobalt, nickel, or mixtures thereof, preferably cobalt and/or nickel. Preferably, a combination of metal components comprising nickel, molybdenum, and tungsten or nickel, cobalt, molybdenum, and tungsten, or cobalt, molybdenum, and tungsten is employed in the process invention.

It is preferred that nickel and/or cobalt make up at least 50 wt. % of the total of Group VIII non-noble metals, more preferably at least 70 wt. %, still more preferably at least 90 wt. %. It may be especially preferred for the Group VIII non-noble metal to consist essentially of nickel and/or cobalt.

It is preferred that molybdenum and tungsten make up at least 50 wt. % of the total of Group VIB metals, more preferably at least 70 wt. %, still more preferably at least 90 wt. %. It may be especially preferred for the Group VIB metal to consist essentially of molybdenum and tungsten.

The molar ratio of Group VIB metals to Group VIII non-noble metals in the catalyst of the invention generally ranges from about 10:1 to about 1:10 and preferably from about 3:1 to about 1:3. The molar ratio of the different Group VIB metals one to the other generally is at this point in time believed not to be critical. When molybdenum and tungsten are employed as Group VIB metals, the molybdenum:tungsten molar ratio preferably lies in the range of about 9:1 to about 1:19, more preferably about 3:1 to about 1:9, most preferably about 3:1 to about 1:6.

The catalyst composition generally comprises at least 50 wt. % of the total of Group VIB and Group VIII metal components, calculated as oxides based on the total weight of the catalyst composition, preferably at least 70 wt. %, more preferably at least 80 wt. %, most preferably at least 90 wt. %, calculated as oxides. The amount of Group VIB metals and Group VIII non-noble metals can be determined via AAS or ICP.

Naphtha feedstocks suitable for hydrodesulfurization comprise one or more natural and/or synthetic hydrocarbons boiling in the range from about 10° C. (50° F.) to about 232° C. (450° F.), at atmospheric pressure. The naphtha feedstock generally contains cracked naphtha, which usually comprises fluid catalytic cracking unit naphtha ("FCC naphtha"), coker naphtha, hydrocracker naphtha, resid hydrotreater naphtha, debutanized natural gasoline ("DNG"), and gasoline blending components from other sources wherein a naphtha boiling range stream can be produced. In an embodiment, the feedstock is selected from FCC naphtha, coker naphtha, and combinations thereof.

In an embodiment, the naphtha feedstock is an FCC naphtha comprising paraffins; naphthenes; aromatics; unsaturates, such as open-chain and cyclic olefins; dienes; and cyclic hydrocarbons with olefinic side chains. The FCC naphtha feedstock generally comprises an overall olefins concentration ranging as high as about 60 wt. %, more typically as high as about 50 wt. %, and most typically from about 4 wt. % to about 40 wt. %. The FCC naphtha feedstock sulfur content will generally range from about 0.05 wt. % to about 0.7 wt. %, and more typically from about 0.07 wt. % to about 0.5 wt. % based on the total weight of the feedstock. Nitrogen content will generally range from about 5 wppm to about 500 wppm, and more typically from about 20 wppm to about 200 wppm. The FCC naphtha typically will have the following additional compositional properties: specific gravity from about 0.7 to about 0.9, API from about 33 to about 41, and aromatics from about 50 to about 90 percent by weight.

In an embodiment, the naphtha feed is a heavy FCC naphtha having a boiling range of from about 127° C. initial boiling point ("IBP") to about 230° C. final boiling point ("FBP"). In other words, the heavy FCC naphtha is a heavy cut of a full-range naphtha. One representative FCC naphtha is characterized by a specific gravity ranging from about 0.8 to about 0.87, API gravity ranging from about 35 to about 39, sulfur from about 0.1 to about 0.7 percent by weight, nitrogen from about 65 to about 85 wppm, aromatics from about 60 to about 90 percent by weight, and olefins from about 4 to about 40 percent by weight. Other heavy FCC naphthas can be used.

The naphtha feed can be treated with hydrogen in the presence of the preferred catalyst in at least one reaction stage, each reaction stage having one or more reactors. Preferred HDS and HDN conditions for the naphtha feed include a reactor pressure of from about 14 bar to about 26 bar, hydrogen pressure from about 8.4 bar to about 15.6 bar, WABT temperature from about 218° C. to about 400° C., a LHSV of about 3.5 to about 6.5 hr$^{-1}$, and a hydrogen to naphtha feed ratio of about 750 standard cubic feet per barrel of naphtha feed (scfb) to about 1430 scfb per barrel of naphtha feed.

More preferably the WABT temperature may range from about 284° C. to about 330° C., and even more preferably from about 305° C to about 315° C. It has been discovered that treating the naphtha feed at the above conditions can substantially remove most of the sulfur and nitrogen compounds providing a naphtha product that is very low in sulfur and nitrogen. More specifically, the inventive method can reduce the amount of sulfur in less about 15 wppm, more preferably less than about 10 wppm and most preferably less than about 5 wppm. It also can reduce the amount of nitrogen to less than about 10 wppm, more preferably to less than about 5 wppm and most preferably less than about 1 wppm.

The preferred hydroprocessing catalyst of any one or more of the reaction zones of any one or more of the hydroprocessing stages are formed form a bulk multimetallic oxide precursor comprised of at least one Group VIII non-noble metal and at least two Group VIB metals, wherein the catalyst composition is made by contacting and reacting insoluble metal salts of the catalyst metals in the presence of a protic liquid. Preferably, the ratio of Group VIB metal to Group VIII non-noble metal may range from about 10:1 to about 1:10. Preferably the precursor is a bulk trimetallic oxide comprised of one Group VIII non-noble metal, preferably Ni or Co and two Group VIB metals, preferably Mo and W. More preferably the ratio of Mo to W is about 9:1 to about 1:9.

The preferred precursor compositions are represented by the formula:

$$(X)_b(Mo)_c(W)_dO_z$$

wherein X is one or more a Group VIII non-noble metal, the molar ratio of b: (c+d) is 0.5/1 to 3/1, preferably 0.75/1 to 1.5/1, more preferably 0.75/1 to 1.25/1; and Z=[2b+6(c+d)]/2.

The molar ratio of c:d is preferably about >0.01/1, more preferably about >0.1/1, still more preferably about 1/10 to about 10/1, still more preferably about 1/3 to about 3/1, most preferably substantially equimolar amounts of Mo and W, e.g., 2/3 to 3/2, and in particular 1:1.

The bulk oxide precursor has a unique x-ray diffraction pattern. While showing crystalline peaks at d=2.53 Å and d=1.70 Å, it should be noted that the overall pattern is characteristic of a disordered material.

The bulk oxide precursor is typically dried before it is processed further. Drying may be conventional, for example at, e.g., temperatures of at least about 225° C., preferably about 250° C. to about 450° C., in a suitable atmosphere, e.g., inerts such as nitrogen, argon, or steam, until drying are substantially complete, i.e., any adsorbed species or substantially completely driven off. Calcination is not required.

The preferred bulk multimetallic oxide precursor may be in the form of a powder having a surface area of at least 50 $m^2/g$ and more preferably of at least 100 $m^2/g$ measured by the B.E.T. method. More particularly, the powder exhibit a pore volume of from about 0.05 to about 5 ml/g, more preferably of about 0.1 to about 4 ml/g, yet more preferably of 0.1 to about 3 ml/g, and most preferably 0.1 to about 2 ml/g determined by nitrogen adsorption. Preferably, pores smaller than 1 nm are not present. Furthermore these particles in the powder preferably have a median diameter of at least 50 nm, more preferably at least about 100 nm, and preferably not more than about 5000 μm and more preferably not more than about 3000 μm. Even more preferably, the median particle diameter lies in the range of about 0.1 to about 50 μm and most preferably in the range of about 0.5 to about 50 μm.

The morphology and texture of the oxide precursor can be controlled by controlling the morphology and texture of the metal source material by the conventional methods.

The oxide precursor may be readily prepared by several methods, including a variation boiling decomposition method used by Teichner and Astier in which a tungsten compound is added to the initial mixture of a molybdenum salt, a nickel salt and ammonium hydroxide. Direct precipitation and pH controlled precipitation in a liquid may also be used to prepare the precursor compound. Preferably a synthesis route using a partially solid or all solid metal compounds in a protic liquid may also be used. It is possible to add the Group VIII non-noble metal containing compound and the Group VIB metal-containing compound in various ways, at various temperatures and pHs, in solution as soluble components, in suspension as insoluble solid components, and as such, simultaneously and/or sequentially.

The preparation methods may involve soluble and insoluble precursors metallic components at high pH. Boiling the resulting solution expels ammonium, reducing the pH, and precipitating the precursor compound.

A partially solid or all solid-metal source route is preferred. Accordingly, solid nickel, molybdenum, and tungsten compounds (sources) are suspended in a single vessel in a protic medium, stirred and heated to form the precursor. Preferably the metal sources should remain at least partially in the solid state during the entire preparation process. Alternatively, at least one of the metal components should remain at least partly in the solid state during the entire process. Thus, at least one metal component remains at least partly in the solid state during the entire "solid" process for making the catalyst. "At least partly," as used in this context, means that at least part of the metal component is present as a solid metal component and, optionally, another part of the metal component is present as a solution of this metal component in the protic medium. For example, a suspension of a metal component in a protic liquid may include the metal at least partly as a solid, and optionally partly dissolved in the protic liquid.

The order of addition of the metal components is not critical. For example, the solid route preparation can be conducted even where component is added simultaneously. The solid route achieves yields approaching quantitative yield, i.e., ~100 wt. %.

It is also believed that for the "solid" and "solid-solute" preparation methods the reaction mechanism preserves to some extent the morphology of the metal source particularly the Group VIII metal source material. To obtain a bulk catalyst composition with high catalytic activity, it is therefore preferred that the metal source materials are porous. Preferably the total pore volume of the metal sources may range from about 0.05 to about 5 ml/g, preferably from about 0.1 to about 4 ml/g, more preferably from about 0.1 to about 3 ml/g, and most preferably from about 0.1 to about 2 ml/g determined by nitrogen adsorption. Pores with a diameter smaller than 1 nm are generally not present in the final catalyst composition. Further, the final catalyst composition may have generally a surface area of at least about 10 $m^2/g$, preferably about 30 $m^2/g$, and more preferably of at least about 50 $m^2/g$, and most preferably of at least about 100 $m^2/g$, determined via the B.E.T. method. For example, nickel carbonate may have a total pore volume of from about 0.19 to about 0.39 ml/g preferably of from about 0.24 to about 0.35 ml/g determined by nitrogen adsorption and a surface area of from about 150 to about 400 $m^2/g$, and more preferably of from about 200 to about 370 $m^2/g$, determined by the B.E.T. method. Furthermore these metal components may preferably have a median particle diameter of at least 50 nm, and not more than 5000 μm, more preferably at least 100 nm, and not more than about 3000 μm. Even more preferably, the median particle diameter may lie in the range of from about 0.1 to about 50 μm, and most preferably in the range of from about 0.5 to about 50 μm.

In general, the metal source materials contain metal and at least one of C, O, and H. Nickel carbonate or cobalt carbonate are preferred metal component to be added at least partly in the solid state because when either carbonate is applied, $CO_2$ evolves and positively influences the pH of the reaction mixture. Further, due to the transformation of carbonate into $CO_2$, the carbonate does not end up in the wastewater.

In the solution route, the metal components are completely dissolved when they are combined and/or reactor to form a precipitate. It is possible, e.g., to combine the metal components when they are already in the dissolved state and then have them react to form a precipitate. However, it is also possible to combine one or more of the metal components which are partly or entirely in the solid state with further metal components. However, in this case, care must be taken that the metal components which are partly or entirely in the solid state will dissolve when present in the reaction mixture. In other words, at least once during the solution route process, all metal components must be present wholly as a solution. Precipitation can be effected by, e.g.:

(a) changing the pH during or after combination of the metal component solutions to such a value that precipitation is induced;

(b) adding a complexing agent during or after combination of the metal component solutions, which complexing agent complexes one or more of the metals to prevent precipitation of the metals, and thereafter changing the reaction conditions, such as temperature or pH, such that the complexing agent releases the metals for precipitation;

(c) adjusting the temperature during or after combination of the metal component solutions to such a value that precipitation is induced;

(d) lowering the amount of solvent during or after combination of the metal component solutions such that precipitation is induced;

(e) adding a non-solvent during or after combination of the metal component solutions to induce precipitation thereof, with a non-solvent meaning that the precipitate is essentially insoluble in this solvent;

(f) adding an excess of either of the components to such an extent that precipitation is induced.

Adjusting the pH in, e.g., option (a) or (b) can be done by adding a base or an acid to the reaction mixture. However, it is also possible to add compounds which upon the temperature increasing will decompose into hydroxide ions or H+ ions, which increase and decrease the pH, respectively. Examples of compounds which will decompose upon the temperature increasing and thereby increase or decrease the pH are urea, nitrites, ammonium cyanate, ammonium hydroxide, and ammonium carbonate.

When solute or solid-solute methods are employed, preferred nickel components which are added in the solute state are water-soluble nickel components, such as, nickel nitrate, nickel sulfate, nickel-nitrate and sulfate acetate, nickel chloride, or mixtures thereof may be used. Preferred molybdenum and tungsten components which are added in the solute state are water-soluble molybdenum and tungsten components such as alkali metal or ammonium molybdate (also peroxo-, di-, tri-, tetra-, hepta-, octa-, or tetra-decamolybdate), Mo—P heteropolyanion compounds, Wo-Si heteropolyanion compounds, W—P heteropolyanion compounds, W—Si heteropolyanion compounds, Ni—Mo—W heteropolyanion compounds, Co—Mo—W heteropolyanion compounds, alkali metal or ammonium tungstates (also meta-, para-, hexa-, or polytungstate), or mixtures thereof.

A preferred combination for the solid method includes using as the metal components at least one of nickel carbonate, tungstic acid and molybdenum oxide. Another preferred combination for a solid-solute route is nickel carbonate, ammonium molybdate and ammonium metatungstate.

Examples of suitable protic liquids include water, carboxylic acids, and alcohols such as methanol or ethanol. Preferably, a liquid comprising water such as mixtures of an alcohol and water and more preferably water is used as protic liquid in this solid route. Also different protic liquids can be applied simultaneously in the solid route. For instance, it is possible to add a suspension of a metal component in ethanol to an aqueous solution of another metal component. In some cases, a metal component can be used which dissolves in its own crystal water (i.e., water of hydration). The crystal water serves as protic liquid in this case. Other protic mediums may also be used.

Preferably, for the solid route a combination of metal components comprising nickel, molybdenum and tungsten or nickel, cobalt, molybdenum and tungsten is applied. For the solid route, where the protic liquid is water, suitable nickel components which are at least partly in the solid state during contacting comprise water-insoluble nickel components such as nickel carbonate, nickel hydroxide, nickel phosphate, nickel phosphite, nickel formate, nickel sulfide, nickel molybdate, nickel tungstate, nickel oxide, nickel alloys such as nickel-molybdenum alloys, Raney nickel, or mixtures thereof Suitable molybdenum components, which are at least partly in the solid state during contacting, comprise water-insoluble molybdenum components such as molybdenum (di- and tri-) oxide, molybdenum carbide, molybdenum nitride, aluminum molybdate, molybdic acid (e.g., $H_2MoO_4$), $MoO_3$, molybdenum sulfide, or mixtures thereof. A suitable soluble chromium source for solid preparation may be ammonium dichromate, while for solution preparation chromic acid. Finally, suitable tungsten components which are at least partly in the solid state during contacting comprise tungsten di- and trioxide, tungsten sulfide ($WS_2$ and $WS_3$), tungsten carbide, tungstic acid (e.g., $H_2WO_4{}^{-H}{}_2O$, $H_2W_4O_{13}$—$9H_2O$), tungsten nitride, aluminum tungstate (also meta-, or polytungstate) or mixtures thereof. These components are generally commercially available or can be prepared by, e.g., precipitation, e.g., nickel carbonate can be prepared from a nickel chloride, sulfate, or nitrate solution by adding an appropriate amount of sodium carbonate. It is generally amount of hydroxygroups. In one embodiment the amount of hydroxy-groups present in the nickel carbonate may be high. For the all solute route a preferred combination is nickel nitrate, ammonium molybdate and ammonium metatungstate.

Preferably, at least 1 wt. %, even more preferably at least 10 wt. %, and still more preferably at least 15 wt. % of a metal component is added in the solid state during the process of the invention, based on the total weight of all Group VIB and Group VIII non-noble metals components, calculated as metal oxides. When it is desired to obtain a high yield, i.e., a high amount of the final catalyst composition, the use of metal components of which a high amount remains in the solid state during the process of the invention may be the preferred method. In that case, low amounts of metal components remain dissolved in the mother liquid and the amount of metal components ending up in the wastewater during the subsequent solid-liquid separation is decreased. Any loss of metal components can be avoided completely if the mother liquid resulting from solid-liquid separation is recycled in the process of the present invention. It is noted that it is a particular advantage of the process of the present invention that compared to a catalyst preparation based on a co-precipitation process, the amount of wastewater can be considerably reduced.

Depending on the reactivity of the metal components, preferably at least 0.01 wt. %, more preferably at least 0.05 wt. %, and most preferably at least 0.1 wt. % of all metal components initially employed in the process of the invention is added as a solution, based on the total weight of all metal components, calculated as metal oxides. In this way, proper contacting of the metal components is ensured. If the reactivity of a particular metal component to be added is low, it is recommended to add a high amount of this metal component as solution.

The catalyst precursor formed in accordance with the solid or solid-solute methods may be used to make hydroprocessing catalysts. For example, the precursors may be sulfided in a liquid or a sulfur-containing stream including in-situ stream to make hydrotreating catalyst. The precursor powder may be used in slurry form or fluidized bed form, and may also be sulfided in-situ or ex-situ. Alternatively, the particles may be composited with a binder before or after sulfiding. Preferably, the catalyst is a bulk catalyst, i.e., the catalyst is not supported.

The precursor can be sulfided or pre-sulfided by a variety of known methods. For example, the composition product can be contacted with a gas comprising $H_2S$ and hydrogen, e.g., 10% $H_2S/H_2$, at elevated temperatures for a period of time sufficient to sulfide the decomposition product, usually at the point of $H_2S$ breakthrough in the exit gas. Sulfiding can also be effected, in situ, by passing a typical feedstock containing sulfur over the decomposition product. Yet another way of sulfiding includes liquid phase presulfidation using conventional sulfidation sources such as dimethyldisulfide or ethyldisulfide or sulfrazol.

The resulting bulk precursor is typically in the form of a powder. The powder may be further processed by, for example, sulfiding. If larger catalyst particles are desired (e.g., in the range of about 1–5 mm) then the particle would be formed before or after sulfidation, preferably before sulfidation, and then sulfided to make the catalyst.

Figure 3:
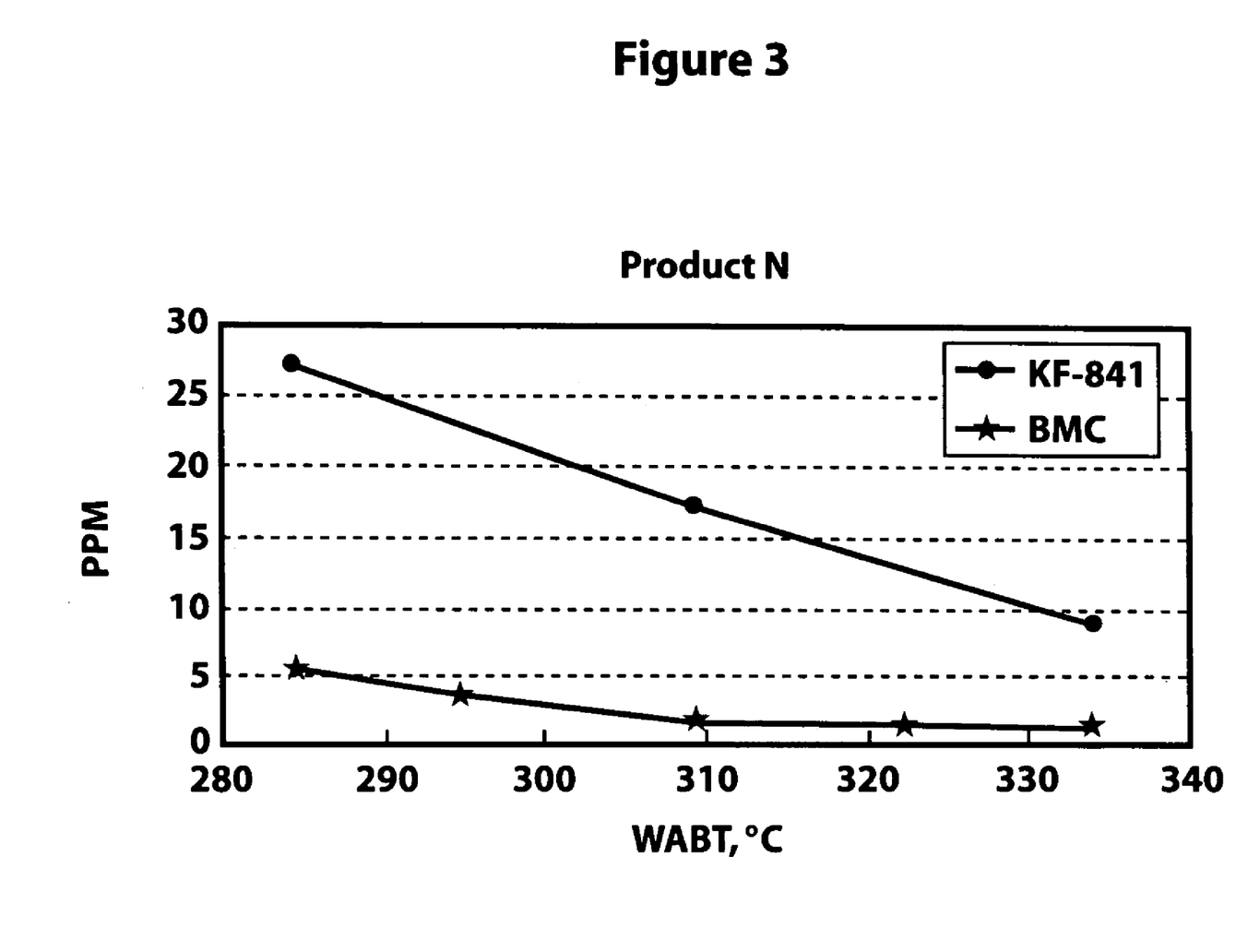
FIGS. 3 and 4 show the amount of nitrogen and sulfur in naphtha, according to an embodiment of the present invention method described in Example 1.

It was found that the bulk multimetallic oxide precursor particles have a characteristic x-ray diffraction pattern which differs from catalysts obtained by co-mixing and conventional hydroprocessing catalysts obtained by impregnation. The x-ray diffraction pattern of the bulk catalyst particles comprises, and preferably essentially consists of, peaks characteristic to the reacted metal components. The resulting bulk catalyst particles are characterized by an x-ray diffraction pattern which comprises peaks at d values. The d values for route 2 and route 3 preparation can be read from FIGS. 4 and 5, respectively. The d values for route 1 preparation are slightly different and the x-ray diffraction pattern has broader peaks as seen in FIG. 3. The catalyst obtained by the solid route has a characteristic x-ray diffraction pattern which differs from catalyst obtained by co-mixing and conventional hydroprocessing catalysts obtained by impregnation. For instance the x-ray diffraction pattern of a Ni—Mo—W precipitate as prepared by the solid route has peaks at d values of 2.53 Å, 1.70 Å and 1.46 Å.

The bulk multimetallic precursor typically is shaped into particles and then sulfided. If the amount of liquid of the bulk precursor is so high that it cannot be directly subjected to a shaping step, a solid liquid separation can be performed before shaping. Optionally the bulk precursor, either as such or after solid liquid separation, can be calcined before shaping.

If a binder material is used in the preparation of the particle, it can be any material that is conventionally applied as a binder in hydroprocessing catalysts. Examples include silica, silica-alumina, such as conventional silica-alumina, silica-coated alumina and alumina-coated silica, alumina such as (pseudo) boehmite, or gibbsite, titania, zirconia, cationic clays or anionic clays such as saponite, bentonite, kaoline, sepiolite or hydrotalcite, or mixtures thereof. Preferred binders are silica, silica-alumina, alumina, titanic, zirconia, or mixtures thereof. These binders may be applied as such or after peptization. It is also possible to apply precursors of these binders that, during the process of the invention, are converted into any of the above-described binders. Suitable precursors are, e.g., alkali metal aluminates (to obtain an alumina binder), water glass (to obtain a silica binder), a mixture of alkali metal aluminates and water glass (to obtain a silica alumina binder), a mixture of sources of a di-, tri-, and/or tetravalent metal such as a mixture of water-soluble salts of magnesium, aluminum and/or silicon (to prepare a cationic clay and/or anionic clay), chlorohydrol, aluminum sulfate, or mixtures thereof.

If desired, the binder material may be composited with a Group VIB metal and/or a Group VIII non-noble metal, prior to being composited with the bulk catalyst composition and/or prior to being added during the preparation thereof. If the binder is peptized, it is also possible to carry out the peptization in the presence of Group VIB and/or Group VIII non-noble metal components.

If alumina is applied as binder, the surface area preferably lies in the range of about 100–400 $m^2/g$, and more preferably about 150–350 $m^2/g$, measured by the B.E.T. method. The pore volume of the alumina is preferably in the range of about 0.5 to about 1.5 ml/g measured by nitrogen adsorption.

Generally, the binder material to be added in the process of the invention has less catalytic activity than the bulk catalyst composition or no catalytic activity at all. Consequently, by adding a binder material, the activity of the bulk catalyst composition may be reduced. Therefore, the amount of binder material to be added in the process of the invention generally depends on the desired activity of the final catalyst composition. Binder amounts ranging from about 0 to about 95 wt. % of the total composition may be used, and typically the amount of the inactive compounds, including binders, would be no more than about 15 wt. %, preferably about 2 to about 15 wt. %. In an unusually high activity embodiment, binder amounts generally range from about 0.5 to about 75 wt. % of the total composition.

It should be noted that the binder as used herein is distinct from supports used in conventional catalyst because the active components are impregnated onto or into the support in a conventional catalyst and here the binder is physically mixed with and composited with the active component.

The precursor can be directly shaped into a particle. Shaping comprises extrusion, pelletizing, beading, and/or spray drying. Shaping can be used, e.g., when the catalyst is to be applied in slurry-type reactors, fluidized beds, moving beds, expanded beds, or ebullating beds, spray drying or beading is generally applied. For fixed bed applications, generally, the precursor is extruded, pelletized and/or beaded. In the latter case, prior to or during the shaping step, any additives that are conventionally used to facilitate shaping can be added. These additives may comprise aluminum stearate, surfactants, graphite or mixtures thereof These additives can be added at any stage prior to the shaping step. Further, when alumina is used as a binder, it may be desirable to add acids prior to the shaping step such as nitric acid to increase the mechanical strength of the extrudates.

It is preferred that a binder material is added prior to the shaping step. Further, it is preferred that the shaping step is carried out in the presence of a liquid, such as water. Preferably, the amount of liquid in the extrusion mixture, expressed as loss on ignition ("LOI") is in the range of 20–80%.

The resulting composited particle composition can, after an optional drying step, be optionally calcined. Calcination however is not essential to the process of the invention. If a calcination is carried out in the process of the invention, it can be done at a temperature of, e.g., from about 100° C. to about 600° C., preferably from about 150° C. to about 550° C., and more preferably from about 150° C. to about 450° C. The drying of shaped particles is generally carried out at temperatures above 100° C.

In a preferred embodiment of the invention, the precursor is subjected to spray drying, (flash) drying, milling, kneading, or combinations thereof prior to shaping by conventional methods. A cracking component may be added during compositing of the particle. The cracking component may serve as an isomerization enhancer. The cracking component can be any conventional cracking component such as cationic clays, anionic clays, zeolites such as ZSM-5, (ultrastable) zeolite Y, zeolite X, ALPO's, SAPO's, amorphous cracking components such as silica-alumina, or mixtures thereof. It will be clear that some materials may act as a binder and a cracking component at the same time. For instance, silica-alumina may have at the same time a cracking and a binding function.

The cracking component, which can comprise about 0 to about 80 wt. %, based on the total weight of the catalyst, can be added at any stage of the process of the present invention prior to the shaping step. However, it is preferred to add the cracking component during the compositing step with the binder.

If desired, further materials can be added in addition to the metal components during particle formation or they may be added during precursor formation. These materials include any material that is added during conventional hydroprocessing catalyst preparation. Suitable examples are phosphorus compounds, boron compounds, fluorine-containing compounds, additional transition metals, rare earth metals, fillers, or mixtures thereof. They may be added during composition during cover by conventional methods. These further materials may include divalent tetra valent, and hexavalent transition metals may be added during precursor synthesis provided the source material is inappropriate for or for solid, solute, or solid-solute synthesis, as desired.

Precursor sulfidation of the composited partial is generally carried out by contacting the composited particle with a sulfur-containing compound such as elementary sulfur, hydrogen sulfide or polysulfides. The sulfidation can generally be carried out after the composited particle has been formed.

If the catalyst composition is used in fixed bed processes, the sulfidation is preferably carried out subsequent to the shaping step and, if applied, subsequent to the last calcination step. Preferably, the sulfidation is carried out ex situ, i.e., the sulfidation is carried out in a separate reactor prior to loading the sulfided catalyst composition into the hydroprocessing unit. Furthermore, it may be desirable that the catalyst composition is both sulfided ex situ and in situ.

The sulfided precursor with this process appears to have high catalytic activity. In contrast to the conventional hydroprocessing catalysts, which usually comprise a carrier impregnated with Group VIII non-noble metals and Group VIB metals, the sulfided precursor can be used without a support. Unsupported catalyst compositions are usually referred to as bulk catalysts.

EXAMPLES

The following examples will serve to illustrate, but not limit, this invention.

Example 1

A naphtha feed high in aromatics and containing significant amounts of nitrogen and sulfur was treated with hydrogen at 20 bar in the presence of an inventive bulk multimetallic catalyst and various reactor temperatures. The naphtha feed quality is provided in Table 1.

The test conditions are provided in Table 2. The test was repeated under the same conditions but using a bulk multimetallic catalyst (BMC). At these conditions, the inventive bulk multimetallic catalyst showed about a 240% HDN activity relative to KF-841. The results are shown in Table 3. The inventive bulk multimetallic catalyst also shows substantial improvement in HDS activity compared to the KF-841 catalyst.

Figure 4:
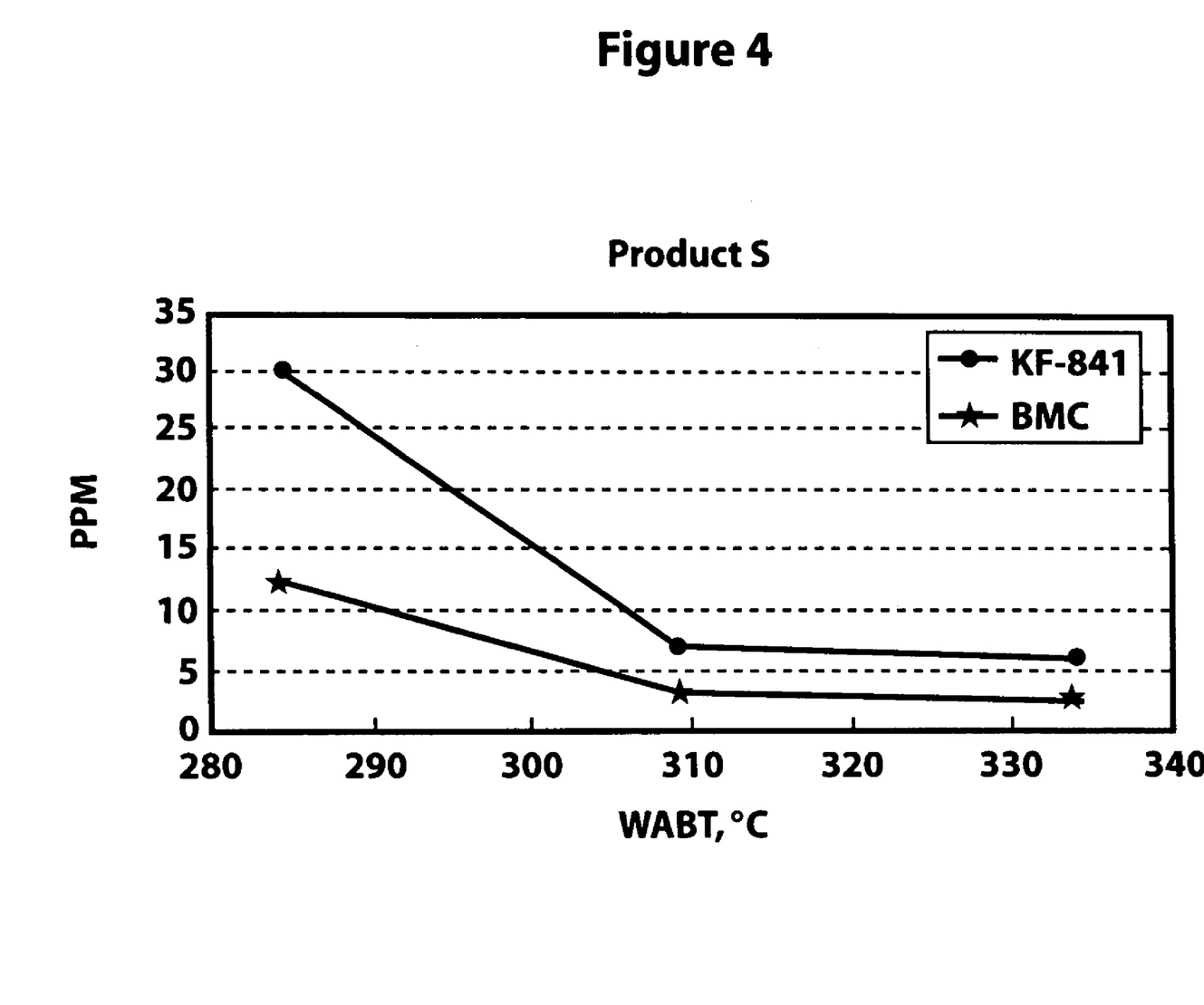

FIGS. 3 and 4 show the amount of nitrogen and sulfur in the treated naphtha, respectively. The data were obtained at various temperatures according to the above test conditions of Example 1 for the KF-841 and the inventive BMC.

The bulk multimetallic catalyst comprised nickel, molybdenum, and tungsten in a molar ratio of 1.5-0.5-0.5, with the metal components, calculated as oxides, making up more than 95% by weight of the catalyst composition.

TABLE 1

Naphtha Feed Quality

| SG | 0.8393 |
|---|---|
| API | 37.1 |
| Sulfur | 0.36 wt.% |
| Nitrogen | 73 ppm |
| Aromatics | 69.4% |
| Olefins | 5.5% |
| IBP | 127° C. (261° F.) |
| FBP | 210° C. (410° F.) |

TABLE 2

Test Conditions

| System pressure | 20 bar (285 psi) |
|---|---|
| H$_2$ purity | 100% |
| Calculated pp H$_2$ | 12 bar (170 psi) |
| WABT | 284–334° C. (543–633° F.) |
| LHSV | 5 hr$^{-1}$ |
| H$_2$/oil | 200 Nl/l (1100 scfb) |

TABLE 3

Relative Volume Activities (RVA)

| Catalyst | RVA HDS | RVA HDN |
|---|---|---|
| KF-841 | 100 | 100 |
| Bulk Multimetallic Catalyst | 116 | 240 |

What is claimed is:

1. A method for upgrading a naphtha feed to a naphtha product containing less than about 10 wppm of nitrogen and less than about 15 wppm sulfur, the method comprising contacting said naphtha feed with hydrogen in the presence of a bulk multimetallic catalyst under effective reactor conditions to hydrodesulfurize and hydrodenitrogenize said naphtha feed to produce said naphtha product, wherein said bulk multimetallic catalyst comprises at least one Group VIII non-noble metal and at least two Group VIB metals.

2. The method of claim 1, wherein said bulk multimetallic catalyst is made by reacting insoluble or partially insoluble metal salts of said metals in the presence of a protic liquid.

3. The method of claim 1, wherein said bulk multimetallic catalyst is made by combining and reacting at least one Group VIII non-noble metal component with at least two Group VIB metal components in the presence of a protic liquid, with at least one of the metal components remaining at least partly in the solid state during the entire catalyst making, said Group VIII and Group VIB metals comprising from about 50 wt. % to about 100 wt. %, calculated as oxides, of the total weight of said bulk catalyst particles, with the solubility of those of the metal components which are at least partly in the solid state during the reaction being less than 0.05 mol/100 ml water at 18° C.

4. The method of claim 1, wherein the bulk multimetallic catalyst is made by combining and/or reacting dissolved metal salts in a protic liquid to form a precipitate.

5. The method of claim 1, wherein said bulk multimetallic catalyst has been subjected to a sulfidation treatment.

6. The method of claim 1, wherein the Group VIII non-noble metal is selected from the group comprising cobalt, nickel, iron, or mixtures thereof, and the Group VIB metals are selected from the group comprising chromium, molybdenum, tungsten or mixtures thereof.

7. The method of claim 1, wherein the Group VIII non-noble metal consists substantially of nickel and the Group VIB metals consist substantially of molybdenum and tungsten.

8. The method of claim 1, wherein the bulk catalyst particles are subjected to one or more of the following process steps:
   (i) compositing with a material selected form the group of binder materials, conventional hydroprocessing catalysts, cracking components, or mixtures thereof,
   (ii) spray-drying, (flash) drying, milling, kneading, slurry-mixing, dry or wet mixing, or combinations thereof,
   (iii) shaping,
   (iv) drying and/or thermally treating, and
   (v) sulfiding.

9. The method of claim 1, wherein said naphtha feed is selected from the group consisting light and full range virgin naphthas, catalytically cracked naphthas, delayed coking naphtha, fluid coking naphtha, and contact coking naphtha.

10. The method of claim 1, wherein said naphtha feed is a heavy catalytically cracked naphtha having a boiling range of from about 250° F. to about 420° F., and comprises aromatics, olefins, sulfur compounds, and nitrogen compounds.

11. The method of claim 1, further comprising a flashing or fractionation step following said hydrotreating step to release any gaseous byproducts and collect the desulfurized and denitrogenized naphtha.

12. The method of claim 1, wherein said effective reactor conditions include a temperature from about 100° C. to about 370° C., a pressure from about 10 to about 60 bar, a hydrogen to naphtha ratio from about 100 to about 2,000 standard cubic feet of hydrogen per barrel of feed, and a space velocity from about 0.5 to about 15 LHSV.

13. A method for upgrading a naphtha feed to a naphtha product containing less than about 10 wppm of nitrogen and less than about 15 wppm sulfur, the method comprising reacting said naphtha in at least one reaction stage, in the presence of a hydrogen containing gas, as it passes through two or more catalyst beds, wherein at least one catalyst bed comprises a nultimetallic catalyst comprising at least one group VIII non-noble metal and at least two Group VIB metals, wherein the ratio of Group VIB metals to Group VII non-noble metals is about 10:1 to about 1:10, and wherein said at least one reaction stage is operated at an effective temperature and hydrogen pressure to hydrodesulfurize and hydrodenitrogenize the naphtha feed to produce said naphtha product.

14. The method of claim 13, wherein said naphtha feed is naphtha from a fluid catalytic cracking unit having a specific gravity from about 0.7 to about 0.9, API from about 33 to about 41, sulfur content from about 0.2 to about 0.5 percent by weight, nitrogen content from about 50 to about 100 wppm, aromatics from about 50 to about 90 percent by weight, and olefins from about 2 to about 9 percent by weight.

15. The method of claim 13, wherein said naphtha feed is naphtha from a fluid catalytic cracking unit having a specific gravity from about 0.8 to about 0.87, API from about 35 to about 39, sulfur content from about 0.3 to about 0.4 percent by weight, nitrogen from about 65 to about 85 wppm, aromatics from about 60 to about 80 percent by weight, and olefins from about 4 to about 7 percent by weight.

16. A two stage method for reducing the sulfur content of a naphtha feed comprising:
   (a) reacting said naphtha feed in a first stage in the presence of a hydrogen-containing treat gas, said first stage containing one or more reaction zones operated under effective conditions and in the presence of at least one first stage catalyst for producing a first liquid product stream having a substantially reduced sulfur content;
   (b) passing said first product stream to a separation zone to form a vapor phase product stream and a second liquid product stream;
   (c) reacting said second liquid product stream in a second stage in the presence of a hydrogen-containing treat gas, said second stage containing one or more reaction zones operated under effective conditions and in the presence of at least one second stage catalyst for producing a naphtha product stream having less than about 15 wppm sulfur; and
   (d) recovering said naphtha product stream.

17. The method of claim 16, wherein said naphtha product stream has less than about 10 wppm sulfur.

18. The method of claim 16, wherein said naphtha product stream has less than about 5 wppm sulfur.

19. The method of claim 16, wherein said at least one of said first stage catalyst or said second stage catalyst is a bulk multimetallic catalyst comprising at least one group non-noble metal and at least two Group VIB metals, wherein the ratio of Group VIB metals to Group VIII non-noble metals is about 10:1 to about 1:10, and wherein said at least one reaction stage is operated at an effective temperature and hydrogen pressure to hydrodesulfurize and hydrodenitrogenize the naphtha feed to produce said naphtha product.

20. The method of claim 16 further comprising a third hydroprocessing stage.

21. The method of claim 16, wherein said bulk multimetallic catalyst is made by reacting insoluble or partially insoluble metal salts of said metals in the presence of a protic liquid.

22. The method of claim 16, wherein said bulk multimetallic catalyst is made by combining and reacting at least one Group VII non-noble metal component with at least two Group VIB metal components in the presence of a protic liquid, with at least one of the metal components remaining at least partly in the solid state during the entire catalyst making, said Group VIII and Group VIB metals comprising from about 50 wt. % to about 100 wt. %, calculated as oxides, of the total weight of said bulk catalyst particles, with the solubility of those of the metal components which are at least partly in the solid state during the reaction being less than 0.05 mol/100 ml water at 18° C.

23. The method of claim 16, wherein said bulk multimetallic catalyst has been subjected to a sulfidation treatment and wherein the Group VIII non-noble metal is selected from the group comprising cobalt, nickel, iron, or mixtures thereof, and the Group VIB metals are selected from the group comprising chromium, molybdenum, tungsten or mixtures thereof.

24. The method of claim 1, wherein said naphtha feed is naphtha from a fluid catalytic cracking unit having a specific gravity from about 0.7 to about 0.9, API from about 33 to about 41, sulfur content from about 0.2 to about 0.5 percent by weight, nitrogen content from about 50 to about 100 wppm, aromatics from about 50 to about 90 percent by weight, and olefins from about 2 to about 9 percent by weight.

25. The method of claim 1, wherein said naphtha feed is naphtha from a fluid catalytic cracking unit having a specific gravity from about 0.8 to about 0.87, API from about 35 to about 39, sulfur content from about 0.3 to about 0.4 percent by weight, nitrogen from about 65 to about 85 wppm, aromatics from about 60 to about 80 percent by weight, and olefins from about 4 to about 7 percent by weight.

* * * * *